(12) United States Patent
Muppa et al.

(10) Patent No.: US 8,859,790 B2
(45) Date of Patent: Oct. 14, 2014

(54) PROCESS FOR THE MANUFACTURE OF A 1,2-EPOXIDE AND A DEVICE FOR CARRYING OUT SAID PROCESS

(75) Inventors: Prasad Muppa, Vondelingenplaat (NL); Ron Postma, Pernis (NL); Bart Van Den Berg, Pernis (NL); Juergen Stock, Frankfurt (DE); Holger Wiederhold, Darmstadt (DE); Hans Rausch, Eschborn (DE); Jorg Schallenberg, Haltern am see (DE); Stefan Bernhardt, Offenbach-Rumpenheim (DE)

(73) Assignee: Momentive Specialty Chemicals Inc., Columbus, OH (US)

( * ) Notice: Subject to any disclaimer, the term of this patent is extended or adjusted under 35 U.S.C. 154(b) by 0 days.

(21) Appl. No.: 13/574,715

(22) PCT Filed: Jan. 26, 2011

(86) PCT No.: PCT/EP2011/000320
§ 371 (c)(1),
(2), (4) Date: Oct. 5, 2012

(87) PCT Pub. No.: WO2011/107188
PCT Pub. Date: Sep. 9, 2011

(65) Prior Publication Data
US 2013/0023680 A1      Jan. 24, 2013

(30) Foreign Application Priority Data
Feb. 2, 2010    (EP) .................................... 10001035

(51) Int. Cl.
*C07D 301/12*    (2006.01)
*B01J 23/32*      (2006.01)
(Continued)

(52) U.S. Cl.
CPC .... *B01J 19/2435* (2013.01); *B01J 2219/00094* (2013.01); *B01D 17/0208* (2013.01); *B01J*
(Continued)

(58) Field of Classification Search
CPC ......................... C07D 301/12; B01J 2231/72
USPC .................................. 549/531; 502/200, 324
See application file for complete search history.

(56) References Cited

U.S. PATENT DOCUMENTS 4,021,454 A    5/1977   Wulff et al.
4,038,291 A *  7/1977   Gipson ......................... 549/530
(Continued)

FOREIGN PATENT DOCUMENTS

CN        1900071       1/2007
DE        19923121      11/2000
(Continued)

OTHER PUBLICATIONS

De Vos et al, Tetra. Let. vol. 39 pp. 3221-3224 (1998).*
(Continued)

*Primary Examiner* — Andrew D Kosar
*Assistant Examiner* — Raymond Covington

(57) ABSTRACT

Apparatus and processes are provided for forming epoxide compounds. In one embodiment, a process for the manufacture of an epoxide is provided including adding an oxidant, a water-soluble manganese complex and a terminal olefin to form a multiphasic reaction mixture, reacting the terminal olefin with the oxidant in the multiphasic reaction mixture having at least one organic phase in the presence of the water-soluble manganese complex, separating the reaction mixture into the at least one organic phase and an aqueous phase, and reusing at least part of the aqueous phase. The invention is also related to a device for performing the above process.

18 Claims, 1 Drawing Sheet

(51) Int. Cl.
*B01J 27/24* (2006.01)
*B01D 17/02* (2006.01)
*B01J 19/24* (2006.01)
*C07D 301/03* (2006.01)
*B01J 4/00* (2006.01)
*B01F 5/06* (2006.01)

(52) U.S. Cl.
CPC ..... 2231/72 (2013.01); *B01F 5/061* (2013.01); *C07D 301/03* (2013.01); *B01J 4/00* (2013.01); *C07D 301/12* (2013.01)
USPC ............................ 549/531; 502/200; 502/324

(56) References Cited

U.S. PATENT DOCUMENTS

| | | | |
|---|---|---|---|
| 4,127,594 | A | 11/1978 | Anderson et al. |
| 4,973,718 | A | 11/1990 | Buchler |
| 5,153,161 | A | 10/1992 | Kerschner et al. |
| 5,155,274 | A | 10/1992 | Herrmann et al. |
| 5,256,779 | A | 10/1993 | Kerschner et al. |
| 5,274,147 | A | 12/1993 | Kerschner et al. |
| 5,329,024 | A | 7/1994 | Jureller et al. |
| 5,429,769 | A | 7/1995 | Nicholson et al. |
| 5,516,738 | A | 5/1996 | Jureller et al. |
| 5,532,389 | A | 7/1996 | Trent et al. |
| 5,833,755 | A | 11/1998 | Schlon et al. |
| 6,054,407 | A | 4/2000 | Schulz et al. |
| 6,087,513 | A | 7/2000 | Liao et al. |
| 6,288,248 | B1 | 9/2001 | Strebelle et al. |
| 6,350,888 | B1 | 2/2002 | Strebelle et al. |
| 6,500,968 | B2 | 12/2002 | Zhou et al. |
| 6,596,883 | B2 | 7/2003 | Hofen et al. |
| 6,673,950 | B1 | 1/2004 | Teles et al. |
| 6,815,552 | B2 | 11/2004 | Strebelle et al. |
| 7,205,419 | B2 | 4/2007 | Strebelle et al. |
| 7,320,779 | B2 | 1/2008 | Strebelle et al. |
| 7,323,578 | B2 | 1/2008 | Catinat et al. |
| 2001/0025695 | A1 | 10/2001 | Patt et al. |
| 2002/0004606 | A1 | 1/2002 | Thiele |
| 2002/0010120 | A1 | 1/2002 | Hage et al. |
| 2006/0167288 | A1 | 7/2006 | Strebelle et al. |
| 2006/0277687 | A1 | 12/2006 | Buhler et al. |
| 2010/0029848 | A1 | 2/2010 | Forlin et al. |
| 2012/0316353 | A1 | 12/2012 | Crampton |

FOREIGN PATENT DOCUMENTS

| | | |
|---|---|---|
| EP | 0458397 | 5/1991 |
| EP | 0458398 | 11/1991 |
| EP | 0618202 A1 | 10/1994 |
| EP | 1403219 | 3/2004 |
| EP | 1883730 | 2/2008 |
| EP | 2149569 A1 | 2/2010 |
| EP | 2149570 A1 | 2/2010 |
| EP | 2285791 A1 | 2/2011 |
| EP | 2343288 A1 | 7/2011 |
| EP | 2354129 A1 | 8/2011 |
| EP | 2354130 A1 | 8/2011 |
| EP | 2354180 A1 | 8/2011 |
| EP | 1299370 B1 | 1/2012 |
| EP | 2402087 | 1/2012 |
| JP | 2002145872 | 5/2002 |
| TW | 305831 | 6/1995 |
| TW | 200823183 | 6/2008 |
| WO | WO 2004/048353 A1 | 6/2004 |
| WO | WO 2005/000827 A1 | 6/2005 |
| WO | WO 2005/095370 A1 | 10/2005 |
| WO | WO 2007/046960 A1 | 4/2007 |
| WO | WO 2008/078861 A1 | 7/2008 |
| WO | WO 2008/087657 A2 | 7/2008 |
| WO | WO 2009/063487 A2 | 5/2009 |
| WO | WO2009/115152 | 9/2009 |
| WO | WO2011/063937 | 6/2011 |
| WO | WO2011/095293 | 8/2011 |
| WO | WO2011/095294 | 8/2011 |
| WO | WO2011/095296 | 8/2011 |

OTHER PUBLICATIONS

Alrich, 1998-1999 pp. 497.*
P.L. Alsters et al., "Fine-Tuning and Recycling of Homogeneous Tungstate and Polytungstate Epoxidation Catalysts", Mechanisms in Homogeneous and Heterogeneous Epoxidation Catalysis (2008) 415-428, Elsevier B.V. and Technology.
I.W.C.E. Arends et al., "Recent developments in selective catalytic epoxidations with H2O2", Topics in Catalysis, vol. 19, No. 1 (2002) 133-141.
T.H. Bennur at al., "Benzylic oxidation with H2O2 catalyzed by Mn complexes of N,N',N''-trimethyl-1,4,7-triazacyclononane: spectroscopic investigations of the active Mn Species", Journal of Molecular Catalysis A: Chemical 185 (2002) 71-80.
N.O. Brace et al., "Hydrophobic Compounds and Polymers from Long Chain Alkanamide-Formaldehyde Condensation Reactions", Journal of Organic Chemistry (1961) vol. 26, 5176-5180.
J. Brinksma at al., "Homogeneous cis-dihydroxylation and epoxidation of olefins with high H2O2 efficiency by mixed manganese/activated carbonyl catalyst system", Tetrahedron Letters 43 (2002) 2619-2622.
A.M. d'A. Rocha Gonsalves et al, "On the mechanism of carboxylic acid co-catalyst assisted metalloporphyrin oxidations" Journal of Molecular Catalysis A: Chemical 168 (2001) 25-32.
J.W. De Boer et al., "The role of salicylic acid, L-ascorbic acid, and oxalic acid in promoting the oxidation of alkenes with H2O2 catalysed by [MnIV2(O)3(tmtacn)2]2+", Royal Society of Chemistry, Dalton Transactions (2008) 6283-6295.
J.W. De Boer, "cis-Dihydroxylation and Epoxidation of Alkenes by Manganese Catalysts Selectivity, Reactivity and Mechanism", Feb. 22, 2008, Dissertation, University of Groningen, PrintPartners Ipskamp BV, Enschede, the Netherlands.
D.E. De Vos et al., "Highly selective olefin epoxidation with manganese triazacyclononane complexes:impact of ligand substitution", Journal of Oganometallic Chemistry 520 (1996) 195-200.
D.E. E Vos at al., "Selective Alkene Oxidation with H2O2 and a Heterogenized Mn Catalyst: Epoxidation and a New Entry to Vicinal cis-Diols", Angew. Chem. Int. Ed. 38, No. 7 (1999) 980-983.
D.E. De Vos et al., "Epoxidation of Terminal or Electron-deficient Olefins with H2O2, catalysed by Mn-trimethyltriazacyclonane Complexes in the Presence of an Oxalate Buffer", Tetrahedron Letters 39 (1998) 3221-3224.
D.E. De Vos et al., "Highly selective epoxidation of alkenes and styrenes with H2O2 and manganese complexes of the cyclic triamine 1,4,7-trimethyl-1,4,7-triazacyclononane", Chem. Commun. (1996) 917-918.
F.C. Frostick Jr. et al., "Synthesis of Some Epoxy Vinyl Monomers by Epoxidation with Peracetic Acid", by J. Am. Chem. Soc. 81 (1958) 3350-3356.
A. Grenz et al., "Synthesis and application of novel catalytically active polymers containing 1,4,7-triazacyclononanes", Chem. Commun. (2001) No. 18, 1726-1727 (Cambridge, England).
R. Hage et al., "Bleach and oxidation catalysis by manganese-1,4,7-triazacyclononane complexes and hydrogen peroxide", Journal of Molecular Catalysis A: Chemical 251 (2006) 150-158.
N. Hoffman et al., "Liquid-Liquid Biphasic, Platinum-Catalyzed Hydrosilylation of AllyL Chloride with Trichlorosilane Using an Ionic Liquid Catalyst Phase in a Continuous Loop Reactor", Adv. Synth. Catal. (2008) 350, 2599-2609.
E. Kaczmarczyk et al., "Selective epoxidation of 1,4-bis(allyloxy)butane to 1-allyloxy-glycidoloxybutane in the presence of ionic liquids", Journal of Molecular Catalysis A: Chemical 265 (2007) 148-152.
E. Kaczmarczyk et al., "Epoxidation of 1,4-bis(allyloxy)butane by hydrogen peroxide using phase transfer catalysis", Journal of Molecular Catalysis A: Chemical 244 (2006) 173-178.
D.E. De Vos et al., Tetrahedron Letters, vol. 39, No. 20, (1998) 3221-3224.

(56) References Cited

OTHER PUBLICATIONS

E. De Vos et al., Journal of the Chemical Society, Chemical Communications, Letchworth, GB, No. 8, (1996) 917-918.

N. Hofmann et al., Advanced Synthesis & Catalysis, vol. 350, No. 16 (2008) 2599-2609.

A. Murphy et al., "Ligand and pH Influence on Manganese-Mediated Peracetic Acid Epoxidation of Terminal Olefins", Organic Letters, (2004) vol. 6 No. 18, 3119-3122.

L. Ningning et al., "Epoxidation of Various Functionalized Olefins by a Ti-MWW/H2O2 Catalytic System", Chin J Catal (2008) vol. 29 Issue 2, 102-104.

G.V. Nizova et al., "Hydrocarbon Oxidations with Hydrogen Peroxide Catalyzed by a Soluble Polymer-Bound Manganese(IV) Complex with 1,4,7-Triazacyclononane", Adv. Synth. Catal. (2002) 344, No. 8, 899-905.

V.C. Quee-Smith et al., "Synthesis, Structure, and Characterization of a Novel Manganese(IV) Monomer, [MnIV(Me3TACN)(OMe)3](PF6) (Me3TACN = N,N',N''-Trimethyl-1,4,7-triazacyclononane), and Its Activity toward Olefin Oxidation with Hydrogen Peroxide", Inorganic Chemistry (1996) vol. 35, No. 22, 6461-6465.

V.B. Romakh et al., "Dinuclear Manganese Complexes Containing Chiral 1,4,7-Triazacyclononane-Derived Ligands and Their Catalytic Potential for the Oxidation of Olefins, Alkanes, and Alcohols", Inorganic Chemistry (2007) vol. 46, No. 4, 1315-1331.

J.Y. Ryu at al., "Alkane Oxidation Catalyzed by Manganese-tmtacn Complexes with H2O2", Bull. Korean Chem. Soc., (2003) vol. 24, No. 12, 1835-1837.

D.C. Sherrington et al., "Polymer-Supported Mo and V Cyclohexene Epoxidation Catalysts: Activation, Activity, and Stability", Journal of Catalysis (1991) vol. 131, 115-126.

G.B. Shul'Pin et al., "Oxidations by the system 'hydrogen Peroxide-[Mn2L2O3][PF6]2 (L=1,4,7-trimethyl-1,4,7-triazacyclononane)-oxalic acid'. Part 6. Oxidation of methane and other alkanes and olefins in water", Journal of Organometallic Chemistry 690 (2005) 4498-4504.

G.B. Shul'Pin et al., "Oxidation with the 'H2O2-maganese(IV) complex-carboxylic acid' reagent", Russian Chemical Bulletin (1998) vol. 47, No. 12, 2379-2386.

K.F. Sibbons et al., "The application of manganese complexes of ligands derived from 1,4,7-triazacyclononane in oxidative catalysis" Dalton Translations (2006) 645-661, The Royal Society of Chemistry, Cambridge, England.

C. Venturello et al., "A New, Effective Catalytic System for Epoxidation of Olefins by Hydrogen Peroxide Under Phase-Transfer Conditions", Journal of Organic Chemistry (1983) vol. 48, No. 21, 3831-3833, American Chemical Society, Easton.

C.B. Woitiski et al., "Oxidations by the system 'hydrogen peroxide-dinuclear manganese(IV) complex-carboxylic acid' Part 5. Epoxidation of olefins including natural terpenes", Journal of Molecular Catalysis A: Chemical 222 (2004) 103-119.

P. Wu et al., "A novel titanosilicate with MWW structure Catalytic properties in selective epoxidation of diallyl ether with hydrogen peroxide" Journal of Catalysis 228 (2004) 183-191.

Z. Xi et al., "An Enviromentally Benign Route for Epochlorohydrin From Allyl Chloride Epoxidation Catalyzed by Heteropolyphophatotungstate", Research on Chemical Intermediates (2007) vol. 33, No. 6, 523-534, VSP.

Aldrich, Catalog Handbook of Fine Chemicals, 1998-1999, p. 497.

R. Mbeleck et al. "Stability and recycling of polymer-supported Mo(VI) alkene epoxidation catalysts", Reactive & Functional Polymers 67 (2007) 1448-1457, Elsevier Science Publishers BV, Netherlands.

E. Kaczmarczyk et al., "Epoxidation of 1,4-diallyloxybutane to 1-allyloxy-4-glycidyloxybutane by the method of phase transfer catalysis", Journal of Molecular Catalysis A: Chemical 235 (2005) 52-56.

Hoffman, Norbert et al., "Liquid-Liquid Biphasic, Platinum-Catalyzed Hydrosilylation of Allyl Chloride with Trichlorosilane Using an Ionic Liquid Catalyst Pahse in a Continuous Loop Reactor" Advanced Synthesis & Catalyst (2008), vol. 350, No. 16, pp. 2599-2609, Wiley-VCH Verlag GmbH & Co. KGaA, Weinheim.

J.W. De Boer, "Mechanism of Cis-Dehydroxylation and Epoxidation of Alkenes by Highly H2O2 Efficient Dinuclear Managanese Catalysts." with Online Supporting Information, Inorganic Chemistry (2007), vol. 46, No. 16, pp. 6353-6372, American Chemical Society.

\* cited by examiner

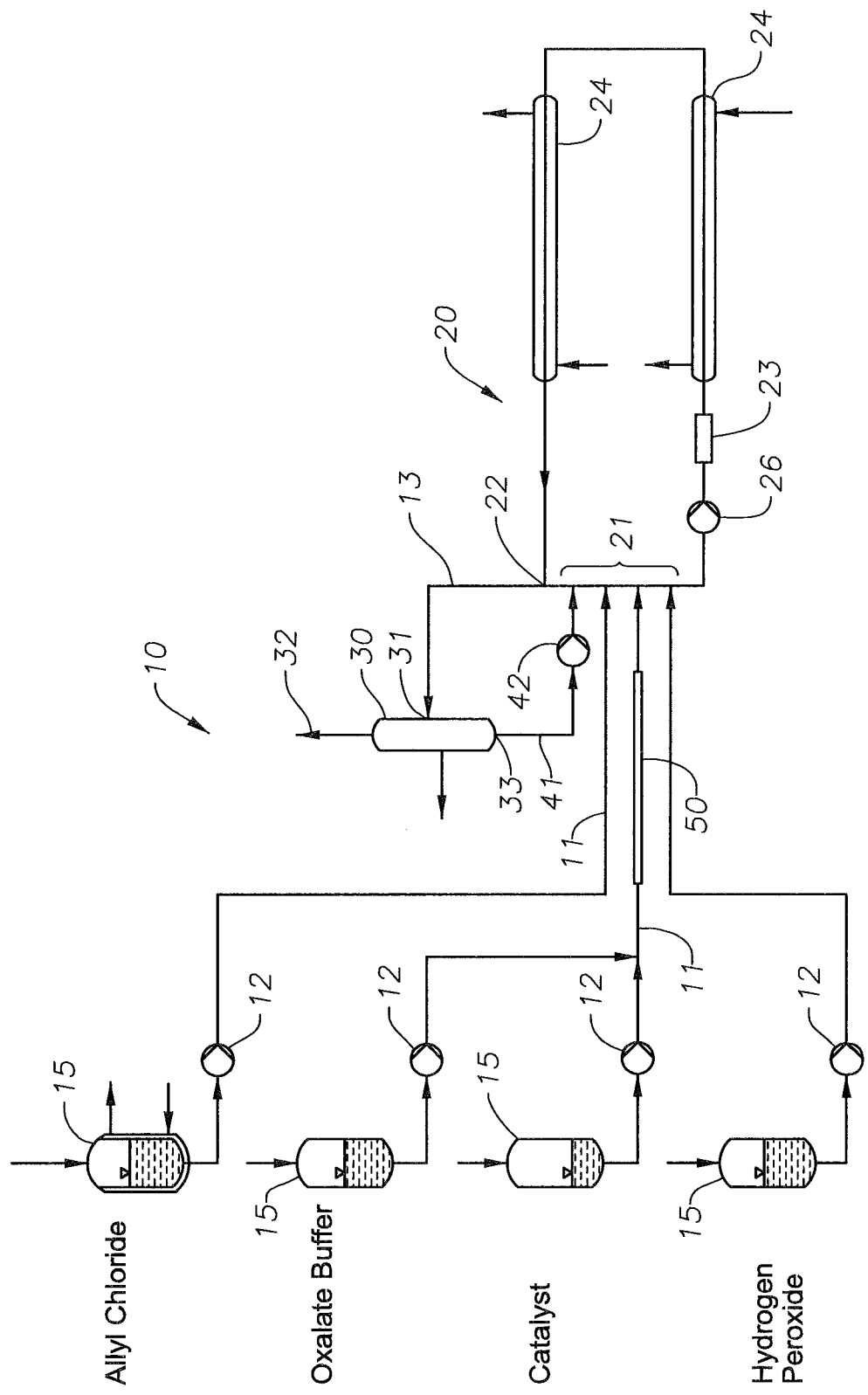

PROCESS FOR THE MANUFACTURE OF A 1,2-EPOXIDE AND A DEVICE FOR CARRYING OUT SAID PROCESS

RELATED APPLICATION DATA

This application claims the benefit of PCT Application PCT/EP2011/000320 with an International Filing Date of Jan. 26, 2011, published as WO 2011/107188, which PCT Application PCT/EP2011/000320 further claims priority to European Patent Application No. EP10001035.4 filed Feb. 2, 2010, the entire contents of both applications are hereby incorporated by reference.

FIELD OF INVENTION

The invention relates to the manufacture of a 1,2-epoxide in the presence of a water-soluble manganese complex as an oxidation catalyst and to a device for carrying out said process.

BACKGROUND OF INVENTION

A process for the manufacture of a 1,2-epoxide is described in the published European patent application EP 2149569. It describes the catalytic oxidation of a terminal olefin using a water soluble manganese complex as the oxidation catalyst.

The process described is carried out in a multiphasic, e.g. biphasic system, i.e. a system comprising an organic phase, which may be a liquid or a gaseous phase, and an aqueous phase. The actual reaction takes place in the aqueous phase, while the resulting epoxide product separates from the aqueous phase into the organic phase due to low solubility of, or extraction or stripping by the organic phase. For this reason, the 1,2-epoxide is produced at high turnover numbers (TON), with high selectivity towards the 1,2-epoxide with moreover improved ease of isolating the produced 1,2-epoxide.

Typically the catalyst system used to achieve the above advantages comprises a manganese atom or a number of manganese atoms coordinated with a ligand or ligands. Of particular interest are binuclear manganese complexes. As an example of the above manufacture of 1,2-epoxide, reference is made to the European patent application publication EP 2149570, which describes the oxidation of allyl chloride to produce epichlorohydrin. EP 2149569 denotes further that the process may be carried out in a reactor, but does not elaborate on this. It turned out, however, that upon isolation of the 1,2-epoxide, an aqueous phase was left which comprised an active catalyst fraction. EP 2149569 does not describe any further use for this fraction, meaning that part of the catalyst is wasted, which is not efficient. Another example about a manufacturing method of propylene oxide is presented in the non-published European patent application 09075528.

DISCLOSURE OF THE INVENTION

It is therefore an object of the current invention to provide a process with improved catalyst efficiency.

It is another object of the invention to provide a process with improved selectivity towards the product.

It is yet another object of the invention to provide a process with low energy requirements for separation and purification steps.

It is still another object of this invention to provide a device, e.g. a reactor, to may out the manufacture of the 1,2-epoxide.

Yet another object if this invention is to provide a reactor which is as small as possible while having the same improved productivity per reactor volume.

One or more of the above objects are achieved by a process for the manufacture of an epoxide, including adding an oxidant, a water-soluble manganese complex, and a terminal olefin to form a multiphasic reaction mixture, wherein the water-soluble manganese complex is a mononuclear species of the general formula (I): $[LMnX_3]Y$ (I), or a binuclear species of the general formula (II): $[LMn(\mu-X)_3MnL](Y)_n$ (II), wherein Mn is a manganese; L or each L independently is a polydentate ligand, each X independently is a coordinating species and each $\mu$-X independently is a bridging coordinating species, and wherein Y is a non-coordinating counter ion, reacting the terminal olefin with, the oxidant in the multiphasic reaction mixture having at least one organic phase in the presence of the water-soluble manganese complex, separating the reaction mixture into the at least one organic phase and an aqueous phase, and reusing at least part of the aqueous phase.

DETAILED DESCRIPTION OF THE FIGURE

The following is a brief description of figures wherein like numbering indicates like elements.

FIG. 1, illustrates a schematic representation of an embodiment of a device for the manufacture of epichlorohydrin.

MODE(S) FOR CARRYING OUT THE INVENTION

The invention is based on the observation that the separated aqueous phase contains catalyst which is still active. This has led the current inventors to the insight that reusing at least part of the separated aqueous phase comprising the catalyst, leads to a more efficient use of the catalyst, and lower energy consumption in subsequent separating steps. The combination of a well dispersed biphasic reaction system and reuse of the aqueous phase may lead to a high turn over number, (TON), which is the number of moles of terminal olefin a mole of catalyst can convert before becoming inactivated. Said combination may further lead to a minimized energy consumption for subsequent separation and purification steps, high selectivity towards product for all raw materials and effective usage of reactor volume leading to a less complicated process. The invention is hereafter discussed in greater detail.

The process is carried out in a multiphasic system of an aqueous phase and at least one organic phase. The oxidation (step a)) of the terminal olefin is believed to take place in an aqueous phase, whereas the organic phase is believed to extract or strip produced 1,2-epoxide from the water phase. The inventors have found that the organic phase contains little or no water soluble byproducts and catalyst. It is beneficial to use a terminal olefin which has limited solubility in water, for example, allyl chloride and allyl acetate instead of conventionally used allyl alcohol. The multiphasic system may be created by adding the terminal olefin with limited solubility to an aqueous phase in an amount greater than what dissolves in the aqueous phase. Preferred terminal olefins have a maximum solubility of about 100 g/L (at 20° C.), more preferably of from 0.01 to 100 g/L.

The volumetric ratio of the organic phase to the aqueous phase, both inside the reactor, and the degree of contact between the phases are important parameters in the performance of the catalyst system. If the amount of organic phase is too high, the aqueous phase is no longer the continuous phase. In this case, there may be insufficient mixing of the ingredients. This means that the conversion rate of terminal olefin is considerably lowered. On the other hand, if the aqueous phase inside the reactor is too high with respect to the amount of organic phase, the terminal olefin concentration in the aqueous phase will be too low with respect to oxidant concentration. This may lead to the production of undesirable side products and catalyst deactivation. Therefore the volumetric ratio of aqueous phase to organic phase inside the reactor is preferably in the range of from 10:1 to 1:5, with emulsion formation as a maximum limit.

The above limitations can also be influenced by the degree of mixing. In practice this means that the organic phase needs to be well dispersed into the continuous aqueous phase, such as in the form of droplets, preferably as small as possible, for example, less than 3 mm.

Upon dispersion of the organic phase into the aqueous phase, the reaction (catalytic oxidation) of the terminal olefin and the oxidant in the presence of the catalyst may occur (step a)). The resulting reaction mixture is discharged from the reactor. The discharged reaction mixture comprises both product and unreacted starting material. The discharged reaction mixture is allowed to settle into its separate phases, the aqueous phase and the at least one organic phase. The at least one organic phase may comprise two organic phases, such as one dispose below and one disposed above the aqueous phase.

The current inventors surprisingly found that the aqueous phase contains catalyst which is still active. The catalyst contained within the separated aqueous phase, can be reused, thereby increasing the catalyst efficiency.

It is believed to be beneficial that the aqueous phase contains at least trace amounts of the terminal olefin. Without being bound to any theory, it is believed that the presence of terminal olefin allows the catalyst to remain active, whereas it is believed that without the presence of terminal olefin and/or due to the presence of the epoxide and/or oxidant without terminal olefin present the activity of the active catalyst reduces. Cooling may also be used to reduce the decrease in catalyst efficiency.

The aqueous phase can be reused by feeding at least a portion (part) of the separated aqueous phase to a next reactor or by recycling at least a portion of the separated aqueous phase to the same reactor (step d)). Preferably, the at least a portion of the aqueous phase is recycled into the reaction mixture. This way, catalyst present in the recycled aqueous phase is not discharged, but efficiently used again.

When the process is running, per unit time, certain volumes of aqueous starting materials, such as the oxidant, catalyst and, if needed, buffer, are supplied to the reaction mixture (step a)).

These aqueous starting materials are indicated as the aqueous components. Simultaneously, per unit time, also a certain volume of separated aqueous phase is recycled into the reaction mixture. The mass ratio of the volume of aqueous components to the volume of recycled aqueous phase added to the reaction mixture at every instant is indicated as the water recycle ratio. In order to achieve the advantageous effects of recycling the catalyst, said water recycle ratio preferably is in the range of from 10:1 to 1:10, more preferably of from 2:1 to 1:5 and most preferably 1:3.5. Also, turbulent conditions such as a high velocity of the aqueous phase will prevent agglomeration of the organic droplets dispersed in said medium.

The molar ratio of terminal olefin to oxidant is very important in the process of the current invention. The molar ratio of terminal olefin to oxidant may be greater than 1:2. Preferably, this ratio is in the range of from 12:1 to 1:1. More preferably, this ratio may be 1:1, 1.2:1, 2:1, or 4:1, or 2:1 to 12:1. If too much oxidant is used, then the selectivity towards the 1,2-epoxide reduces due to the production of undesirable side-products. Another consequence of too much oxidant with respect to terminal olefin is rapid catalyst deactivation. If not enough oxidant is used, then the turnover number is suboptimal. This is therefore significantly different from bleaching conditions described in the prior art, where excessive amounts of oxidant, i.e. hydrogen peroxide are used. To ensure optimal peroxide efficiency, the oxidant is preferably added to the aqueous phase at a rate about equal to the reaction rate of the catalytic oxidation.

The reaction (catalytic oxidation) is carried out using hydrogen peroxide, or a precursor thereof, as an oxidant. Hydrogen peroxide has strong oxidizing properties. It is typically used in an aqueous solution. The concentration of hydrogen peroxide may vary, from 15% (e.g., consumer grade for bleaching hair) to 98% (propellant grade), with a preference for industrial grades varying from 30 to 70%. More preferably, the concentration of hydrogen peroxide is 70%. Other oxidants that may be used include organic peroxides, peracids, and combinations thereof.

The reaction (catalytic oxidation) of the terminal olefin takes place in the aqueous phase. The aqueous phase may have a pH from 1 to 8, such as from 2 to 5. The aqueous phase may further comprise a buffer system to stabilize the pH in a certain range. For instance, it has been found advantageous that the aqueous phase is stabilized in a pH range of from 1 to 8, more preferably of from 2 to 5. The pH is therefore (well) below that used when bleaching olefins with hydrogen peroxide as the oxidant, typically carried out at more alkaline conditions (e.g., pH adjusted with $NaHCO_3$ to 9.0). The suitable or preferred range may be achieved by several known acid-salt combinations, with the preferred combination being based on oxalic acid-oxalate salt, acetic acid-acetate salt, malonic acid-malonate salt, and combinations thereof.

The aqueous phase may further comprise minor amounts, if any, of other organic compounds. The aqueous phase may also contain minor amounts of co-solvents, e.g. to increase the solubility of the olefin. Suitable co-solvents include, for example, acetone, methanol, and other water-soluble alcohols. Co-solvents may be used in amounts such as to keep a biphasic system, preferably in an amount <10 weight percent.

The aqueous phase may further comprise a phase transfer agent and/or a surfactant, in particular if a terminal olefin is used with low solubility (e.g., below 0.1 g/L water). Known phase transfer agents that may be used in the process of the invention include quaternary alkyl ammonium salts. Known surfactants that may be used in the process of the invention include non ionic surfactants such as Triton X100™ available from Union Carbide.

The catalyst system comprising a water soluble manganese complex is described as follows. The oxidation catalyst is a water soluble manganese complex. Advantageously, the manganese complexes include mononuclear species of the general formula (I):

and binuclear species of the general formula (II):

wherein Mn is a manganese; L or each L independently is a polydentate ligand, preferably a cyclic or acyclic compound containing 3 nitrogen atoms; each X is independently a coordinating species and each μ–X is independently a bridging coordinating species, selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, OCN⁻, and $S_4^{2-}$ and combinations thereof, wherein R is a $C_1$-$C_{20}$ radical selected from the group consisting of alkyl, cycloalkyl, aryl, benzyl and combinations thereof, and Y is a non-coordinating counter ion selected from the group consisting of RO⁻, Cl⁻, Br⁻, I⁻, F⁻, $SO_4^{2-}$, RCOO⁻, $PF_6^-$, acetate, tosylate, triflate ($CF_3SO_3^-$) and a combination thereof with R once again being a $C_1$ to $C_{20}$ radical selected from the group consisting of alkyl, cycloalkyl, aryl, benzyl and combination thereof. The non-coordinating counter ion Y may provide for the charge neutrality of the complex and the value of n depends upon the charge of the cationic complex and anionic counter ion Y, for example, n may be 1 or 2. In one embodiment, an ion of $CH_3COO^-$ or $PF_6^-$ may be used as the non-coordinating counter ion. Ligands which are suitable for the present invention are acyclic compounds containing at least 7 atoms in the backbone or cyclic compounds containing at least 9 atoms in the ring, each having the nitrogen atoms separated by at least two carbon atoms. A preferred class of ligands is that based on (substituted) triazacyclononane ("Tacn"). The preferred ligand is 1,4,7-trimethyl-1,4,7,-triazacyclononane ("TmTacn").

Dinuclear manganese complexes are denoted as preferred, because of their greater activity and solubility in water. Preferred dinuclear manganese complexes are those of the formula [$Mn^{IV}_2(\mu\text{-}O)_3L_2$](Y)$_n$ (same as formula: [$LMn(\mu\text{-}O)_3MnL$](Y)$_n$), wherein n is 2, and L and Y have the meaning identified above, preferably TmTacn as ligand, and $PF_6^-$ or acetate ($CH_3CO_2^-$, hereinafter OAc) as counterion. The catalyst system comprising a water soluble manganese complex is described above. The preferred complex for the current invention comprises 1,4,7-trimethyl-1,4,7,-triazacyclononane ("TmTacn") as the preferred ligand or ligands. This ligand is commercially available from Aldrich.

The manganese complex is used in catalytically effective amounts. Typically, the catalyst is used in a molar ratio of catalyst (Mn) to the oxidant of from 1:10 to 1:10,000,000, preferably of from 1:100 to 1:1,000,000, most preferably of from 1:1000 to 1:100,000. As a matter of convenience the amount of catalyst may also be expressed in terms of its concentration, when keeping in mind the volume of the aqueous medium. For instance, it may be used in a molar concentration (based on the Mn) of from 0.001 to 10 mmol/L, preferred of from 0.01 to 7 mmol/L and most preferably of from 0.01 to 2 mmol/L.

The reaction conditions for the catalytic oxidation may be quickly determined by a person skilled in the art. The reaction is exothermic, and cooling of the reaction mixture may be required. The reaction is preferably carried out at temperatures anywhere from –5° C. to 40° C., dependent upon such physical parameters as melting and boiling point of the used terminal olefins.

According to the invention, the terminal olefin used is an epoxidizible olefin which may be functionalized. The terminal olefin may be a liquid under process conditions, e.g., allyl chloride or liquefied propylene, but also a gas, e.g. gaseous propylene.

Examples of suitable terminal olefins include terminal olefinically unsaturated compounds. In one embodiment, the terminal olefinically unsaturated compound may have at least one unsaturated —C═C— bond, such as at least one unsaturated —C═CH₂ group. The olefinically unsaturated compound may comprise more than one unsaturated —C═C— bond. Moreover, the unsaturated —C═C— bond need not be a terminal group. Terminally olefinically unsaturated compounds may have one or more terminal —C═CH₂ bonds.

Suitable examples of terminal olefinically unsaturated compounds therefore include the following compounds:

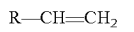

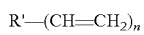

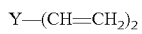

wherein R is a radical of 1 or more carbon atoms optionally comprising 1 or more heteroatoms (such as oxygen, nitrogen or silicon); R' is a multivalent radical of 1 or more carbon atoms optionally comprising 1 or more heteroatoms wherein n corresponds with the valence of the multivalent radical; X is a halogen atom, and Y is an oxygen atom.

Of particular interest are olefinically unsaturated compounds selected from the compounds:
(a) vinylchloride or allylchloride;
(b) 1-alkene, preferably propene:
(c) mono-, di- or polyallyl ethers of mono-, di- or polyols;
(d) mono-, di- or polyvinyl ethers of mono-, di- or polyols;
(e) mono-, di- or polyallyl esters of mono-, di- or polyacid;
(f) mono-, di- or polyvinyl esters of mono-, di- or polyacids;
(g) divinylether or diallylether.

The terminal olefin may have limited solubility in water, for example, the terminal olefin may have a maximum solubility in the aqueous phase at 20° C. of about 100 g/L, more preferably of from 0.01 to 100 g/L at 20° C.

In a more preferred embodiment of the present invention, the terminal olefin is selected from allyl bromide, allyl chloride and allyl acetate. In a most preferred embodiment of the invention allyl chloride is used for the manufacture of epichlorohydrin, because of the commercial interest and ease of isolating the produced epichlorohydrin.

According to another preferred embodiment of the present invention the terminal olefin is propylene in order to produce propylene oxide, and the reaction is carried out at temperatures in the range from –5° C. to 40° C. Propylene is preferably used in excess over the oxidant.

According to still another embodiment of the invention, the buffer, if any, and oxidation catalyst are fed as a pre-mixed mixture into step a).

Another aspect of the invention is related to a device carrying out the above process for the manufacture of 1,2-epoxide. According to the invention, the device comprises a reactor for performing the catalytic oxidation having an inlet for feeding the oxidant, the oxidation catalyst, optionally a buffer and the terminal olefin to the reactor, and an outlet for discharging the reaction mixture from said reactor, separating means connected to the reactor outlet for separating the reaction mixture into the at least one organic phase and an aqueous phase, recycling means for recycling part of the aqueous phase separated in the separating means, dispersing means for dispersing the terminal olefin into the aqueous phase and cooling means for controlling the temperature of the catalytic oxidation process.

According to the invention, the device comprises a reactor for carrying out the process having an inlet and an outlet. Via the reactor inlet the reactants are fed to the reactor, whereas via the reactor outlet the reaction mixture is discharged. The device farther comprises separating means connected to the reactor outlet for separating the reaction mixture into the at least one organic phase and the aqueous phase as explained above. Preferably, this separation means comprises a straight forward liquid to liquid separator, such as a settling tank, since the product forms at least one separate organic phase which phase separates from the aqueous phase when allowed to settle. Other devices such as hydrocyclones can also be used.

The aqueous phase is recycled into the reactor via the inlet of the reactor. This recycling means may be of simple design, e.g. a pipe connecting an aqueous phase outlet of the separation means and the reactor inlet equipped with a pump to transport the aqueous phase into the reactor. It is noted here that the skilled person will be aware that the reactor according to the invention is equipped with standard process technological elements like e.g. pumps, valves and control mechanisms.

The reactor according to the invention further comprises dispersing means for dispersing the organic terminal olefin phase into the aqueous phase and cooling means for controlling the temperature of the catalytic oxidation, because of its exothermic nature.

About the reactor type, several reactor designs are suited to carry out the process according to the invention. The reactor may be a plug flow reactor (PFR). Due to the required high velocity for dispersing and the long residence times a PFR used in the present invention will be a very long PFR. The reactor may also be a continuous stirred tank reactor (CSTR). When using a CSTR, special care should be taken in dispersing the terminal olefin into the aqueous phase.

According to a preferred embodiment of the invention, the catalytic oxidation may also be carried out in a loop reactor. In a loop reactor, the reaction mixture is circulated. When the circulation rate of the loop reactor is about 15 times the rate at which the aqueous components and the terminal olefin is fed, i.e. the feed rate, the loop reactor can be described as a CSTR because of the high degree of back mixing. The advantage of using a loop reactor in the present process is that it allows for the well defined mixing behaviour of a pumped system combined with dispersing means in a compact reactor design.

According to yet another preferred embodiment of the invention the dispersing means is a static mixer, since this mixer will provide maximum break up of organic droplets in the continuous aqueous phase.

According to another embodiment of the invention fresh oxidant and olefin are fed to the aqueous phase in subdivided portions to the reactor through multiple inlet parts distributed over the reactor housing.

The present invention is further explained by means of FIG. 1, which shows a schematic representation of an embodiment of a device for the manufacture of epichlorohydrin.

It is noted here that the skilled person facing the task of constructing the device for carrying out the process according to the invention, will be aware that all process technological elements of the device are constructed and operated by using common general process technological knowledge.

In this embodiment, the device 10 comprises a loop reactor 20 comprising an inlet 21 and an outlet 22. Hydrogen peroxide, a water soluble manganese complex as the oxidation catalyst, an oxalate buffer solution and allyl chloride, which are disposed in separate feeding tanks 15, are fed to the reactor 20. The reactants are transported from the feeding tanks 15 to the reactor inlet 21 through feeding conduits 11 by means of feeding pumps 12. A pre-mixing means 50 may be disposed between the inlet 21 and one or more of the feeding pumps 12 to pre-mix some of the components, such as the catalyst and oxalate buffer in FIG. 1. The reactor inlet 21 advantageously comprises several inlet ports, one port for each reactant. The reaction mixture is discharged from the reactor 20 via the reactor outlet 22 into a separating means 30. The reactor outlet 22 and separating means 30 are connected via a discharge conduit 13. The separating means 30 comprises a separation inlet 31 through which the reaction mixture is supplied to the separating means 30. In the separating means 30 the at least one organic phase and the aqueous phase are allowed to phase separate. The organic phase comprising epichlorohydrin is isolated from the separating means 30 through the product outlet 32.

At least part of the aqueous phase in the separating means 30 is recycled to the reactor 20 via a recycling conduit 41 connecting a recycling outlet 33 of separating means 30 and reactor inlet 21. A recycling pump 42 is comprised in the recycling conduit 41 to transport the aqueous phase. The organic phase inside the reactor 20 is dispersed in the aqueous phase using a dispersing means 23. The reactor 20 further comprises a reactor pump 26 for transporting the reaction mixture and cooling means 24 to cool the reaction mixture. Said cooling means 24 may be e.g. a water cooler or other types of heat exchanging means. However, the choice of the type of cooling means 24 is left to the expertise of the skilled person.

What is claimed is:

1. A process for the manufacture of an epoxide, comprising:
   a) adding an oxidant, a water-soluble manganese complex, and a terminal olefin to form a multiphasic reaction mixture comprising at least one organic phase and an aqueous phase, wherein the water-soluble manganese complex is a mononuclear species of the general formula (I):

$$[LMnX_3]Y \qquad (I)$$

or a binuclear species of the general formula (II):

$$[LMn(\mu-X)_3MnL](Y)_n \qquad (II)$$

wherein Mn is a manganese; L or each L independently is a polydentate ligand, each X independently is a coordinating species and each μ–X independently is a bridging coordinating species, and wherein Y is a non-coordinating counter ion;
   b) reacting the terminal olefin with the oxidant in the multiphasic reaction mixture having at least one organic phase in the presence of the water-soluble manganese complex;
   c) separating the at least one organic phase and the aqueous phase, wherein the aqueous phase comprises the water-soluble manganese complex; and
   d) reusing at least part of the aqueous phase.

2. The process according to claim 1, wherein step a) comprises the sub steps of:
   a1) adding to the reaction mixture the oxidant and the water-soluble manganese complex as aqueous phase components; and
   a2) dispersing the terminal olefin into the aqueous phase.

3. The process of claim 1, wherein the reaction takes place in an aqueous phase of the multiphasic reaction mixture.

4. The process of claim 1, wherein the reusing at least part of the aqueous phase comprises at least a portion of the aqueous phase obtained in step c) is recycled into step a).

5. The process of claim 2, wherein the water recycle ratio of aqueous components to reused aqueous phase is in the range of from 10:1 to 1:10.

6. The process according to claim 5, wherein the water recycle ratio is about 1:3.5.

7. The process of claim 1, wherein the molar ratio of terminal olefin to oxidant is in the range of from 12:1 to 1:1.

8. The process of claim 1, wherein the terminal olefin has a maximum solubility at 20° C. of about 100 g/L.

9. The process of claim 1, wherein the aqueous phase further comprises a buffer system and a pH in the range of from 1 to 8, and the buffer is added to the reaction mixture as an aqueous component.

10. The process of claim 1, wherein the reaction is carried out at temperatures in the range of from −5° C. to 40° C.

11. The process of claim 1, wherein the terminal olefin is selected from allyl bromide, allyl chloride and allyl acetate and the reaction is carried out at temperatures in the range from −5° C. to 40° C.

12. The process of claim 1, wherein the terminal olefin is propylene and the reaction is carried out at temperatures in the range from −5° C. to 40° C.

13. The process of claim 1, wherein the molar ratio of water-soluble manganese complex to oxidant is in the range of from 1:10 to 1:10,000,000.

14. The process of claim 1, wherein the oxidant is hydrogen peroxide or a precursor thereof.

15. The process of claim 1, wherein the aqueous phase comprises a pH in the range of from 1 to 5.

16. The process of claim 1, wherein each X is independently selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, and $S_4^{2-}$ and combinations thereof, and R is selected from the group consisting of $C_1$-$C_{20}$ alkyl, $C_1$-$C_{20}$ cycloalkyl, $C_1$-$C_{20}$ aryl, benzyl and combinations thereof.

17. The process of claim 1, wherein each μ–X is independently selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, and $S_4^{2-}$ and combinations thereof, and R is selected from the group consisting of $C_1$-$C_{20}$ alkyl, $C_1$-$C_{20}$ cycloalkyl, $C_1$-$C_{20}$ aryl, benzyl and combinations thereof.

18. The process of claim 1, wherein Y is a non-coordinating counter ion selected from the group consisting of $RO^-$, $Cl^-$, $Br^-$, $I^-$, $F^-$, $SO_4^{2-}$, $RCOO^-$, $PF_6^-$, acetate, tosylate, triflate, and a combination thereof, and R is selected from the group consisting of $C_1$-$C_{20}$ alkyl, $C_1$-$C_{20}$ cycloalkyl, $C_1$-$C_{20}$ aryl, benzyl and combination thereof.

\* \* \* \* \*